United States Patent [19]

Baglioni

[11] Patent Number: 4,521,538

[45] Date of Patent: Jun. 4, 1985

[54] ESTER OF THE 1-METHYL-5-P-TOLUOYLPYRROLE-2-ACETIC ACID HAVING ANTIINFLAMMATORY, MUCOLYTIC AND ANTITUSSIVE PROPERTIES, PROCESS FOR ITS PREPARATION AND PHARMACEUTICAL COMPOSITIONS CONTAINING THEM

[75] Inventor: Alessandro Baglioni, Rome, Italy

[73] Assignee: Medosan Industrie Biochimiche Riunite S.p.A., Albano Laziale, Italy

[21] Appl. No.: 472,255

[22] Filed: Mar. 4, 1983

[30] Foreign Application Priority Data

Mar. 5, 1982 [IT] Italy ............................. 47938 A/82

[51] Int. Cl.³ ............... C07D 207/323; A61K 31/40
[52] U.S. Cl. ..................................... 514/423; 548/539
[58] Field of Search ..................... 548/539; 424/274

[56] References Cited

U.S. PATENT DOCUMENTS

| 3,752,826 | 8/1973 | Carson | 548/539 |
| 4,284,785 | 8/1981 | Hanifin, Jr. et al. | 548/248 |
| 4,379,793 | 4/1983 | Calzada Badia et al. | 548/539 |
| 4,396,626 | 8/1983 | Ward et al. | 548/539 |

FOREIGN PATENT DOCUMENTS 6845 1/1980 European Pat. Off. .

OTHER PUBLICATIONS

Baiocchi et al., Chem. Abstracts, vol. 90:54686e (1979).
Rojo et al., Chem. Abstracts, vol. 91:13488u (1979).
Carenini et al., Chem. Abstracts, vol. 91 (1979), p. 469, Abstract #4999j.

Primary Examiner—Donald G. Daus
Assistant Examiner—William A. Teoli, Jr.
Attorney, Agent, or Firm—Cushman, Darby & Cushman

[57] ABSTRACT 1-methyl-5-p-toluoylpyrrole-2-acetic acid guaiacyl ester, which possesses antiinflammatory, antipyretic, mucolytic and antitussive properties, is disclosed.

This ester is prepared by reacting guaiacol with an activated derivative of the 1-methyl-5-p-toluoylpyrrole-2-acetic acid of formula

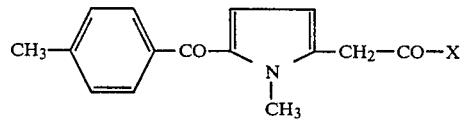

wherein X is an activating group suitable for promoting the formation of an ester bond.

3 Claims, No Drawings

ESTER OF THE 1-METHYL-5-P-TOLUOYLPYRROLE-2-ACETIC ACID HAVING ANTIINFLAMMATORY, MUCOLYTIC AND ANTITUSSIVE PROPERTIES, PROCESS FOR ITS PREPARATION AND PHARMACEUTICAL COMPOSITIONS CONTAINING THEM

The present invention relates to 1-methyl-5-p-toluoylpyrrole-2-acetic acid guaiacyl ester having formula

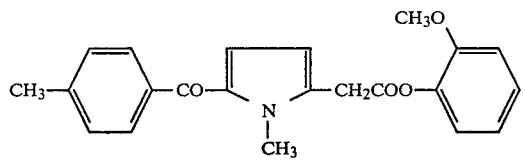

which possesses valuable antiinflammatory, analgesic antipyretic, mucolytic and antitussive properties.

The present invention also relates to a process for preparing this ester and to orally or parenterally administrable pharmaceutical compositions containing same. This compound is very effective in the treatment of any pathological conditions, whether acute or chronic, of the upper airways when these are affected by inflammatory and catarrhal conditions and accompanied by pain and fever.

The ester of this invention can be prepared by esterifying 1-methyl-5-p-toluoylpyrrole-2-acetic acid with guaiacol (2-methoxyphenol) in the presence of a suitable condensing agent and, optionally, of a catalyst.

More specifically, the process of this invention comprises:

reacting guaiacol with an activated derivative of the 1-methyl-5-p-toluoylpyrrole-2-acetic acid of general formula

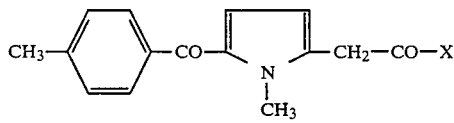

wherein X is an activating group suitable for promoting the formation of an ester bond with guaiacol at a temperature comprised between about 0° C. and 35° C., in the presence of either aprotic or protic solvents depending on the nature of the activating group Suitable activated derivatives of formula

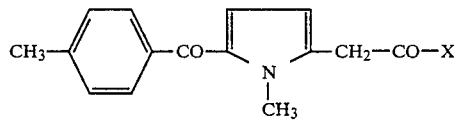

are those wherein X is selected from the group consisting of the halogen atoms (preferably chlorine), the

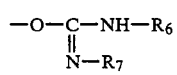

residue, wherein $R_6$ and $R_7$ are alkyl radicals having from 1 to 3 carbon atoms or cycloalkyl radicals having from 5 to 6 carbon atoms, preferably cyclohexyl, and the

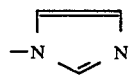

residue.

All these activated derivatives can be prepared by well-known procedures.

When X is halogen (e.g. chlorine), the corresponding activated derivative can be prepared by halogenating (e.g. chlorinating) 1-methyl-5-p-toluoylpyrrole-2-acetic acid.

When X is the

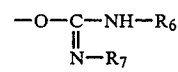

residue (preferably, $R_6=R_7=$cyclohexyl), the corresponding activated derivative is prepared by condensing 1-methyl-5-p-toluoylpyrrole-2-acetic acid with an N,N'-dialkylcarbodiimide (preferably, N,N'-dicyclohexylcarbodiimide). This condensation reaction can be suitably carried out in the presence of a catalyst, such as p-toluensulfonic acid, 4-dimethylaminopyridine and 4-(1-pyrrolidinyl) pyridine.

When X is the

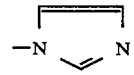

residue, the corresponding activated derivative is prepared by condensing 1-methyl-5-p-toluoylpyrrole-2-acetic acid with N,N'-carbonyldiimidazole. This condensation reaction can be suitably carried out in the presence of a catalyst, such as sodium or magnesium ethylate.

The process is generally carried out in a nonpolar environment, although water-dioxane and water-tetrahydrofuran mixtures can be employed with N,N'-dicyclohexyl-carbodiimide is used as condensing agent, in the presence or absence of a catalyst. Preferred solvents are the following: dichloromethane, dichloroethane, tetrahydrofuran, dioxane, dimethyl-sulfoxide and N,N-dimethylformamide.

The preparation of the ester according to this invention is illustrated by the following example.

EXAMPLE

Preparation of 1-methyl-5-p-toluoylpyrrole-2-acetic acid guaiacyl ester

To a solution of 5.14 g (0.02 mole) of 1-methyl-5-p-toluoylpyrrole-2-acetic acid in 200 ml of dichloromethane, cooled on an ice bath and kept under vigorous stirring, there was firstly added a solution of 4.4 g (0.022 moles) of dicyclohexylcarbodiimide in 40 ml of dichloromethane, then a solution of 2.8 g (0.024 moles) of guaiacol in 40 ml of the same solvent and, finally, a solution of 300 mg of 4 (1-pyrrolidinyl) pyridine in 40 ml of dichloromethane. The resulting mixture was kept under stirring at 0°C.–5° C. for 0.5 hour, then under stirring at room temperature for 3.5 hours.

The precipitate of N,N'-dicyclohexylurea which formed (4 g) was filtered off and the filtrate was evaporated under vacuum. The residue was taken up with ethyl acetate (300 ml) and the organic solution was transferred into a separatory funnel and first washed with a solution of 5% acetic acid (50 ml) to remove the catalyst, then with 2N NaOH (2×25 ml) to remove the unreacted starting acid and guaiacol, and finally washed with a saturated solution of sodium chloride till neutrality. After drying on anhydrous sodium sulfate, the mixture was filtered and the solvent removed under vacuum. An oil was obtained, which was chromatographed on silica using benzene as eluant. After solvent removal from the collected eluates, about 5.5 g of a yellowish oil were obtained, which solidified spontaneously. This product, taken up with a small amount of cyclohexane and filtered, gave a colourless solid product (5 g; 69.4% of the theoretical value) having melting point 95°–96° C. After crystallization from cyclohexane, an analysis sample of 1-methyl-5-p-toluoylpyrrole-2-acetic acid guaiacyl ester had melting point 98°–99° C.

Analysis: $C_{22}H_{21}NO_4$; calculated % C 72.71; H 5.82; N 3.85. found % C 72.79; H 5.81; N 4.00. corresponding to the compound having formula

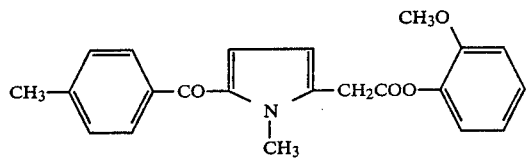

Its chemico-physical characteristics are as follows:
Empyrical formula: $C_{22}H_{21}NO_4$
Molecular weight: 363.40

Melting point: 98°–99° C. (from cyclohexane)
Yield: 69.4% of the theoretical value
Solubility: soluble in the usual organic solvents
IR and NMR spectra confirm that this ester compound possesses the above-identified structure.

PHARMACOLOGICAL PROPERTIES

The experiments carried out with the 1-methyl-5-p-toluoylpyrrole-2-acetic acid guaiacyl ester show that this product possesses pharmacological properties suitable for therapeutic application in some pathological conditions. The composition that had been administered via the oral and/or parenteral route, was in suspension of 0.5% carboxymethylcellulose in neutral pH physiological saline solution. In particular the compound of this invention exhibited an inhibiting action against acute inflammation concomitantly to a marked analgesic action. It has also been demonstrated, as described below, that this compound has a considerable antithermic activity, and in vivo tests show good mucolytic and antitussive activity. All these pharmacotherapeutic effects were obtained with doses and administration regimens that did not provoke significant toxic effects. It was also shown that this compound can be perfectly tolerated by the gastrointestinal tract. Doses, the routes of administration and in general the methods whereby the effects on animals are obtained suggest that this compound can be useful in human therapy for pathological situations characterized by phlogosis and pain. As an example the experimental data are described below of the activity of the compound of this invention compared with that of the 1-mehtyl-5-p-toluoyl-2-acetic acid sodium salt dihydrate (tolmetin $Na.2H_2O$), at equimolecular doses, and also with that of indomethacin in the antiinflammatory test.

Antiinflammatory activity

This effect was evaluated by means of an experimental model reproducing acute inflammation in rats: for this purpose the carrageenin-induced oedema test was employed following the method described by C. A. Winter (J. Pharmac. Exp. Ther. 141: 369, 1963) using as reference substances of known antiinflammatory acitivity: indomethacin and tolmetin $Na.2H_2O$ S. Wong, J. F. Gardocki and T. P. Pruss, J. Pharmac. Exp. Ther. 185 (1): 127, 1973).

Table I lists the tested compounds, the concentration thereof, routes of administration and relative percentage oedema inhibitions; the data are commented upon at the end of the Tables.

TABLE I

| | | OEDEMA % INHIBITION | | | | | | | |
|---|---|---|---|---|---|---|---|---|---|
| Antiinflammatory activity of 1-methyl-5-p-toluoylpyrrole-2-acetic acid guaiacyl ester | | | | | | | | | |
| | DOSE | per os | | | | i.p. | | | |
| COMPOUNDS | mg/kg | 2 h | 4 h | 6 h | 24 h | 2 h | 4 h | 6 h | 24 h |
| Indomethacin | 2.5 | 18.6 | 20.7 | 19.2 | 2.6 | 21.0 | 20.0 | 17.0 | 2.5 |
| " | 5 | 26.3 | 29.1 | 28.5 | 2.7 | 30.0 | 29.0 | 23.0 | 3.4 |
| " | 10 | 48.2 | 49.0 | 46.0 | 7.9 | 49.7 | 46.0 | 48.1 | 8.0 |
| Tolmetin $Na.2H_2O$ | 25 | 24.6 | 26.2 | 30.1 | 6.2 | 28.0 | 29.1 | 32.1 | 8.9 |
| " | 50 | 43.1 | 46.0 | 41.3 | 9.1 | 47.0 | 49.1 | 40.0 | 7.1 |
| " | 100 | 60.8 | 60.0 | 64.5 | 14.6 | 64.1 | 65.8 | 60.2 | 11.2 |
| 1-methyl-5-p-toluoyl-pyrrole-2-acetic acid guaiacyl ester | 25 | 27.0 | 29.0 | 28.0 | 3.2 | 33.5 | 30.0 | 25.0 | 7.0 |
| | 50 | 49.0 | 53.0 | 51.0 | 5.3 | 55.0 | 51.6 | 49.0 | 9.2 |
| | 100 | 71.6 | 77.8 | 77.0 | 7.2 | 80.0 | 78.0 | 70.0 | 9.5 |

Analgesic activity

By means of the phenylquinone-induced writhing test (abdominal contractions) described by E. Siegmund (Proc. Soc. Exp. Biol. Med. 95: 729, 1957) the analgesic activity of 1-methyl-5-p-toluoylpyrrole-2-acetic acid guaiacyl ester was evaluated.

The inhibiting effect on the abdominal contractions induced by phenyl-p-quinone was calculated by the following formula:

$$\% \text{ protection} = \frac{\text{no. of contractions in controls} - \text{no. of contractions in treated rats}}{\text{no. of contractions in controls}} \times 100$$

Table II lists the doses, routes of administration and their efficacy expressed as percentage of protection.

TABLE II

Analgesic activity of 1-methyl-5-p-toluoyl-pyrrole-2-acetic acid guaiacyl ester

| COMPOUNDS | DOSE mg/kg | % PROTECTION per os | % PROTECTION i.p. |
|---|---|---|---|
| Vehicle | — | 0.0 | 0.0 |
| Tolmetin Na.2H₂O | 5 | 15.0 | 16.5 |
| " | 10 | 40.6 | 46.2 |
| " | 20 | 62.0 | 69.1 |
| 1-methyl-5-p-toluoyl pyrrole-2-acetic acid guaiacyl ester | 5 | 30.0 | 30.0 |
| | 10 | 58.6 | 62.5 |
| | 20 | 79.4 | 78.0 |

Antipyretic activity

In order to determine this activity, hyperthermia was induced in albino male Wistar rats weighing 250±10 g by intraperitoneally injecting 10 ml/kg of a 1.5% suspension of dry, purified brewer' yeast (Carlo Erba). The substance used for comparison was tolmetin Na.2H₂0 the antipyretic activity whereof is well known (S. Wong, S. F. Gardocki and T. P. Pruss, J. Pharmac. Exp. Ther. 185(1): 127, 1973).

TABLE III

Antipyretic activity of 1-methyl-5-p-toluoyl-pyrrole-2-acetic acid guaiacyl ester

| COMPOUNDS | DOSE mg/kg | % temperature decrease per os 1 h | 2 h | 3 h | i.p. 1 h | 2 h | 3 h |
|---|---|---|---|---|---|---|---|
| Tolmetin Na.2H₂O | 50 | 12.0 | 20.0 | 29.5 | 15.0 | 19.0 | 30.5 |
| Tolmetin Na.2H₂O | 75 | 13.0 | 26.0 | 27.0 | 18.0 | 29.0 | 34.0 |
| Tolmetin Na.H₂O | 100 | 18.0 | 30.9 | 47.0 | 28.0 | 39.0 | 51.0 |
| 1-methyl-5-p-toluoylpyrrole-2-acetic acid guaiacyl ester | 50 | 16.0 | 20.0 | 33.0 | 18.0 | 26.0 | 39.0 |
| | 75 | 18.0 | 27.0 | 49.0 | 30.0 | 35.0 | 56.0 |
| | 100 | 29.0 | 35.0 | 50.0 | 42.0 | 49.0 | 58.0 |

Mucolytic activity

The experiment was carried out "in vitro" according to the method of R. S. Hirsch (Bull. Physio-path. resp., 9: 435, 1973) for the purpose of investigating the effect of 1-methyl-5-toluoylpyrrole-2-acetic acid guaiacyl ester on the consistency of human expectoration collected from patients suffering from chronic bronchopulmonary diseases.

Table IV lists the percentage decrease of the expectoration consistency provoked by the compound of this invention in comparison with dithiothreitol and acetylcysteine which are known mucolytic agents.

TABLE IV

Mucolytic activity of 1-methyl-5-p-toluoylpyrrole-2-acetic acid guaiacyl ester

| COMPOUNDS | DOSE | No. of experiments | % decrease of expectoration consistency |
|---|---|---|---|
| Dithiothreitol | 0.1 M (1.5%) | 12 | 90 |
| acetylcysteine | 1.2 M (20.0%) | 12 | 81 |
| 1-methyl-5-p-toluoyl-pyrrole-2-acetic acid guaiacyl ester | 1.0 M (9%) | 12 | 52 |

Antitussive activity

The antitussive effect on albino male Guinea-pigs weighing 300 g was evaluated using the method described by Y. Kasé (Selected Pharmacological Testing Methods, p. 363, Marcel Dekker Inc., New York, 1968).

TABLE V

Antitussive activity of 1-methyl-5-p-toluoyl-pyrrole-2-acetic acid guaiacyl ester.
% variations of the kymograph plot concerning amplitude and frequency of coughs

| COMPOUNDS | DOSE mg/kg | % INHIBITION per os amplitude | frequency | i.p. amplitude | frequency |
|---|---|---|---|---|---|
| Tolmetin Na.2H₂O | 50 | 0 | 0 | 0 | 0 |
| " | 75 | 7 | 0 | 0 | 10 |
| " | 100 | 5 | 5 | 7 | 10 |
| 1-methyl-5-p-toluoyl pyrrole-2-acetic acid guaiacyl ester | 50 | 16 | 22 | 18 | 26 |
| | 75 | 19 | 45 | 25 | 50 |
| | 100 | 38 | 56 | 40 | 55 |

Ulcerogenic activity

Male Wistar rats weighing 180 g were randomized into groups of 10. Three doses of each compound were administered. One group received the vehicle alone (10 ml/kg b.w.). Each dose was given orally for four days consecutively and the rats were sacrificed on the fifth day for necropsy. The ulcerogenic effect was evaluated by the following scale:

number of lesions:
(1) each haemorrhagic point at least 1 mm in diameter was scored as 1 lesion,
(2) haemorrhagic points less than 1 mm in diameter were scored in the following manner:
  (a) 1 to 9 = one lesion
  (b) 10 to 19 = two lesions
  (c) 20 to 29 = three lesions
severity of lesions:
(1) no lesion: 0
(2) gastric mucosal irritation without haemorrhage: 1
(3) haemorrhagic points less than 1 mm in diameter: 2
(4) haemorrhagic points between 1 and 3 mm in diameter: 3
(5) haemorrhagic points larger than 3 mm in diameter: 4
(6) perforations 5

By means of this scale it was possible to obtain the gastric damage index:

$$I = \text{mean no. of lesions} + \text{mean of severity} + \%\,\frac{\text{incidence}}{10}$$

The results are given in Table VI.

TABLE VI

Ulcerogenic activity of 1-methyl-5-p-toluoylpyrrole-2-acetic acid guaiacyl ester

| COMPOUNDS | DOSE mg/kg | mean No. of lesions | mean severity | % incidence 10 | gastric damage index |
|---|---|---|---|---|---|
| Vehicle | — | 1 | 1 | 6 | 8 |
| Tolmetin Na.2H₂O | 50 | 2 | 2 | 7 | 11 |
| Tolmetin Na.2H₂O | 100 | 2.5 | 3.5 | 10 | 16 |
| Tolmetin Na.2H₂O | 200 | 3 | 4 | 10 | 17 |
| 1-methyl-5-p-toluoylpyrrole-2-acetic acid guaiacyl ester | 50 | 1 | 1 | 7 | 9 |
| | 100 | 1 | 2 | 8 | 11 |
| | 200 | 2 | 2 | 8 | 12 |

Toxicity

Acute toxicity of 1-methyl-5-p-toluoylpyrrole-2-acetic acid guaiacyl ester was determined in two animal species, i.e. in albino male Swiss mice (23±1 g) and male Wistar rats (110 g) via the oral and intraperitoneal routes. Table VII lists the LD$_{50}$ values (mg/kg).

TABLE VII

| | Acute toxicity of 1-methyl-5-p-toluoylpyrrole-2-acetic acid guaiacyl ester | | |
|---|---|---|---|
| COMPOUNDS | Animal species | LD$_{50}$ (mg/kg) per os | i.p. |
| Tolmetin | Mice | 802 | 550 |
| | Rats | 827 | 612 |
| 1-methyl-5-p-toluoylpyrrole-2-acetic acid guaiacyl ester | Mice | >1500 | 1200 |
| | Rats | >1500 | 1175 |

The data given in Tables I–VII show the considerable pharmaco-therapeutical effect of 1-methyl-5-p-toluoylpyrrole-2-acetic acid guaiacyl ester at the tested doses and in comparison with the control products. The low toxicity of the above compound confers to it a high therapeutical index: in fact it may be observed that the acute toxicity values (Table VII) are of several magnitudes higher than those used for reaching pharmacologically active doses. Moreover, it is interesting to observe that the ulcerogenic effect is moderate as regards the number of gastric lesions and their severity (Table VI) contrary to antiinflammatory agents in general which produce a marked ulcerogenic effect. Administration to healthy animals at the doses and routes used in the experiments did not provoke death in the long- or short-term treatments nor apparent signs of toxic effects. The results given in Tables I–VII witness the therapeutical interest of the pharmaceutical composition of the present invention.

The patients in need of an antiinflammatory, analgesic, antipyretic, mucolytic and antitussive pharmaceutical composition will be orally or parenterally administered a therapeutically effective amount 1-methyl-5-p-toluoylpyrrole-2-acetic acid guaiacyl ester.

The dose of this compound orally or parenterally administered will be generally comprised between about 2 and about 15 mg/kg of body weight/day, although larger or smaller doses can be administered by the attending physician having regard to the age, weight and general conditions of the patient, utilizing sound professional judgement.

In practice, the compound is orally or parenterally administered in any of the usual pharmaceutical forms which are prepared by conventional procedures well-known to those persons skilled in the pharmaceutical technology. These forms include solid and liquid unit dosage forms such as tablets, capsules, suppositories, solutions, syrups and the like as well as injectable forms, such as sterile solutions for ampoules and phials. Hereinbelow some non-limiting examples of compositions suitable for oral or parenteral administration are given.

| PHARMACEUTICAL COMPOSITIONS | |
|---|---|
| (1) CAPSULE | |
| Each capsule contains: active principle | 200 mg |
| excipients: | |
| starch | 48 mg |
| lactose | 143 mg |
| magnesium stearate | 1.5 mg |
| sodium lauryl sulfate | 0.2 mg |
| (2) INJECTABLE PHIAL (3 ml) | |
| Each phial contains: active principle | 175 mg |
| excipients: | |
| propylene glycol | 250 mg |
| sodium metabisulfite | 9 mg |
| sodium hydroxide | 3.6 mg |
| lidocaine hydrochloride | 10 mg |
| sterile bidistilled water | balance to 3 ml |
| (3) SUPPOSITORY | |
| Each suppository contains: active principle | 200 mg |
| excipients: | |
| mixture of triglycerides of vegetal saturated fatty acids | 750 mg |
| polysorbate | 250 mg |

What is claimed is:

1. A compound, 1-methyl-5-p-toluoylpyrrole-2-acetic acid guaiacyl ester having the formula

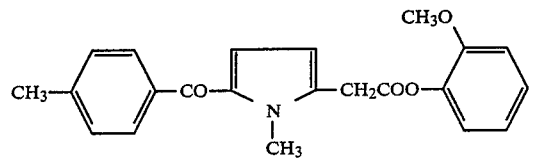

2. An orally or parenterally administrable pharmaceutical composition suitable for use as antiinflammatory, analgesic, antipyretic, mucolytic or antitussive comprising a therapeutically effective amount of 1-methyl-5-p-toluoylpyrrole-2-acetic acid guaiacyl ester and a pharmacologically acceptable excipient therefor.

3. A process for the therapeutic treatment of a patient in need of an antiinflammatory, analgesic, antipyretic, mucolytic and antitussive comprising administering to the patient an amount of 1-methyl-5-p-toluoylpyrrole-2-acetic acid guaiacyl ester effective for such purpose.

* * * * *